United States Patent [19]

Bernhardsson et al.

[11] 4,214,951
[45] Jul. 29, 1980

[54] METHOD AND APPARATUS FOR DETERMINING CRITICAL TEMPERATURES FOR CORROSION

[76] Inventors: Sven-Olof Bernhardsson, Västerled 108B; Stig A. Alfredsson, Trollstigen 3, both of 811 00 Sandviken, Sweden

[21] Appl. No.: 914,178

[22] Filed: Jun. 9, 1978

[30] Foreign Application Priority Data

Jun. 10, 1977 [SE] Sweden .............................. 7706789

[51] Int. Cl.$^2$ ........................................... G01N 27/46
[52] U.S. Cl. .................................. 204/1 T; 204/195 C
[58] Field of Search ............. 204/1 C, 195 C; 324/29, 324/71 R

[56] References Cited

PUBLICATIONS

"Corrosion, vol. 2," Edited by L. L. Shreir, 2nd Edition (1976), pp. 20:126–20:132.

Primary Examiner—Aaron Weisstuch

[57] ABSTRACT

The temperature of a corrosive electrolyte is changed in steps, and the critical temperature of corrosion of a test material is measured in terms of the temperature at which the current or voltage between an electrode of the material being tested and another electrode in the corrosive electrolyte takes a noticeable jump in value.

14 Claims, 2 Drawing Figures

ELECTRIC CONNECTION ——————
THERMAL CONNECTION  — — — — —

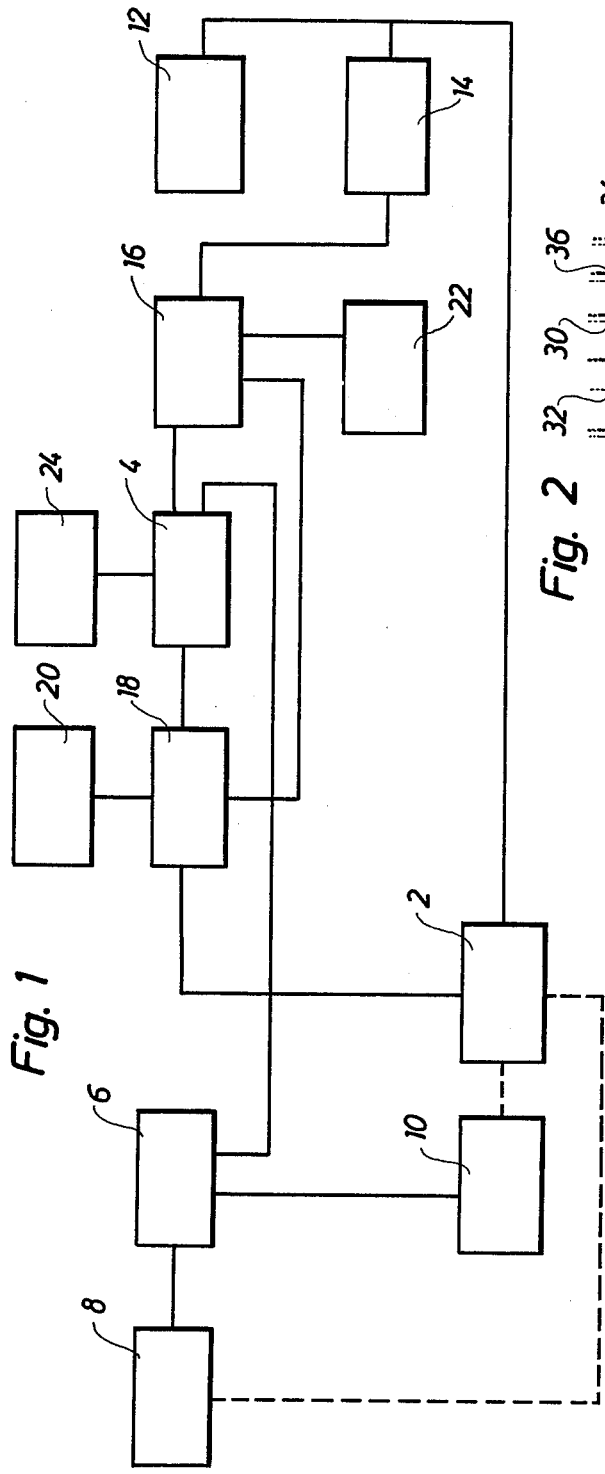
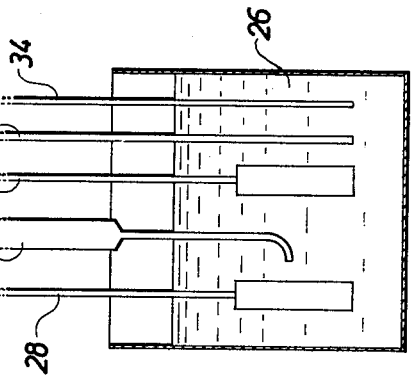

METHOD AND APPARATUS FOR DETERMINING CRITICAL TEMPERATURES FOR CORROSION

The present invention relates to a method of determining critical temperatures for corrosion and an apparatus for automatically carrying out the method.

The most commonly used method at present for determining the resistance in an acid solution of a metal or an alloy that can be passivated, for instance a stainless steel, consists in performing so-called weight loss measurements. In that method samples or specimens are weighed after preparation, immersed in the solution for a certain time period and then weighed again, whereafter the corrosion rate can be calculated. Generally a corrosion rate of 0.1 mm/year is considered to be the limit for usability of stainless steel. The testing is generally performed during 1+3+3 days and nights for each concentration and temperature, which requires four weighings and therefore is a laborious operation. Besides, for each concentration and temperature the samples or specimens are renewed.

The temperature is a critical factor for corrosion resistance of metals due to its influence on corrosion processes and solubilities, e.g. of oxygen. An increased temperature may lead to a strongly increased corrosion; and there exists a critical temperature for corrosion. Thus, the critical temperature is that temperature, at which the material no longer is passive but is dissolved at a rate exceeding e.g. 0.1 mm/year, see above.

There exists a critical temperature, not only for corrosion in acid solutions, but also for corrosion in neutral, chloride containing solutions.

In addition to determination by weight loss measurements, the critical temperature can also be determined by potentiostatic studies. An example of such a method is described in West German Patent 951 785.

However, that previously known method is very laborious, expensive, and time consuming, as a large number of tests must be performed at different temperatures in order to obtain the critical temperature. In addition, the obtained results are often difficult to evaluate.

The purpose of the present invention is to avoid these disadvantages of the prior art and provide a method and an apparatus for rapid and efficient determination of the critical temperature for corrosion of metals and alloys which can be passivated.

This purpose is achieved by a method in which the temperature of an electrolyte in which test, counter, and reference electrodes are submerged, is adjusted to a predetermined value: whereafter the potential difference between the test and reference electrodes or the current intensity between the test and counter electrodes at constant potential difference between the test and reference electrodes is measured and compared with a preset reference voltage or current value.

In response to said comarison, either the adjusted temperature is recorded as the critical temperature, or the temperature of the electrolyte is altered and the measuring and the comparison process is repeated by an apparatus comprising a test electrode, a counter electrode, and a reference electrode submerged in an electrolyte. A temperature adjusting unit is disposed for adjusting the temperature of the electrolyte to a predetermined value and a comparator unit is arranged to compare the potential difference between the test and reference electrodes or the current intensity between the test and counter electrodes at constant potential difference between the test and reference electrodes with a preset reference voltage- or current value and to deliver an output signal, which in response to this comparison either actuates an indicator to indicate that the temperature of the electrolyte is equal to the critical temperature or triggers the temperature adjusting unit to alter the temperature of the electrolyte. The corrosion potential is that potential at which the anodic process (=corrosion process) is equal to the cathodic process (e.g. reduction of $O_2$ or $H^+$). The invention is based on the fact that, if the metal is passive, that is, the corrosion rate is low, the corrosion potential is high. Oppositely, if the metal is active, that is, the corrosion rate is high, the corrosion potential is low. Thus, by measuring the corrosion potential with respect to a reference electrode it is possible to indirectly determine the corrosion rate. The difference between the corrosion potential in active and passive states amounts to several hundred millivolts, i.e. sufficiently large to be distinct and quite unambiquous. Further, the corrosion rate is either very high or very low and at the transition between active and passive state the corrosion rate is changed by a jump.

Consequently, the critical temperature can be redefined as the temperature at which
 (a) The potential of a material with respect to a reference electrode in a corrosive electrolyte; is below a certain valve, or
 (b) The corrosion rate (=the current) exceeds a certain value, at a substantially constant potential with respect to a reference electrode in a corrosive electrolyte.

In the present invention either of the conditions (a) and (b) above can be freely chosen as definition of the critical temperature, and by continuous monitoring of the potential or corrosion rate (the current) during the course of the measurement information is immediately obtained about when the critical temperature is reached.

In neutral chloride containing solutions the pitting corrosion potential of metals and alloys which can be passivated shows a strong dependence on the temperature in a certain interval of the temperature. That temperature at which the temperature dependence is strongest is called the critical pitting temperature. This temperature varies with the composition of the material and the composition of the solution. Conventionally, this critical temperature is determined by determining the pitting corrosion potential for a number of different temperatures, which procedure requires extensive testing. Instead of varying the potential at different temperatures, the temperature is varied at a fixed high potential in the method and the apparatus according to the present invention. This gives a more rapid and a more reliable determination of the critical pitting temperature.

Thus, the method and the apparatus according to the invention is useful for rapid and easy determination of critical temperatures for corrosion of all metals and alloys which can be passivated, such as stainless steels, aluminum alloys, nickel alloys, iron and titanium and for materials coated by such metals and alloys.

An embodiment of the invention chosen as an example will be described below with reference to the drawings, in which FIG. 1 is a block diagram of the apparatus according to the invention, and FIG. 2 an outline diagram of the measuring cell, the sensing member of the temperature transmitter, and the source of heat in the apparatus according to FIG. 1.

As shown in FIG. 2, the material to be studied is submerged in an electrolyte 26 in a measuring cell, which electrolyte can be an acid or another corrosive solution. The material thus forms test electrode 28. The measuring cell further comprises a counter electrode 30 submerged in the same electrolyte, which counter electrode may be of the same material as the sample or specimen or of another material. A suitable material for the counter electrode is platinum. The measuring cell also includes a reference electrode 32.

The initial temperature of the electrolyte is adjusted by a temperature adjusting unit, comprising a programming unit 4, a regulator 6 and a temperature transmitter 8. The programming unit 4 delivers to the regulator 6 a signal representing a desired value of the temperature of the electrolyte. The temperature transmitter 8 senses the acutal temperature with a temperature sensing member 34, see FIG. 2, and delivers continuously to the regulator a signal corresponding to the actual temperature. In response to these two signals the regulator controls, by a source of heat 10, the temperature of the electrolyte in such a manner that it assumes the desired value. The source of heat may preferably consist of an immersion heater, shown as 36 in FIG. 2.

When the desired initial temperature is reached the sample or specimen is activated by connecting a potentiostat 12 or a galvanostat 14 for a time interval preset by a time relay 16.

After this activation the potential difference between the test electrode 28 and the reference electrode 32 is measured and supplied to a comparator unit 18, in which the potential difference is compared with a refernce voltage value. Means 20 are connected to the comparator for arbitrarily adjusting this reference value.

If the measured potential difference reaches the reference value before the end of the time interval determined by a second time relay 22, the comparator 18 will trigger the programming unit 4 for delivering to the regulator 6 a signal representing a higher temperature of the electrolyte. After the electrolyte has been adjusted to this new temperature the sample or specimen is re-activated and the measuring and comparison process is repeated. This procedure is repeated automatically until such a temperature is reached that the measured potential difference does not reach the reference level before the end of the time interval. The programming unit 4 then actuates an indicator 24 at the end of the interval for recording this temperature as the critical temperature. Thus, this temperature is the one at which passivation of the metal or alloy of the specimen no longer occurs in the electrolyte 26.

The complete method described above is automatically controlled by the programming unit 4. The temperature of the electrolyte is preferably always increased in equal steps. The size of the temperature step is freely adjustable in the programming unit 4 and is preferably of the order of 1°–10° C.

The measurements can also begin at a high temperature of the electrolyte, which temperature is gradually decreased. In this embodiment the comparator 18 is constructed to trigger the programming unit 4 at the end of the interval determined by the time relay 22 to deliver to the regulator 6 a signal representing a lower temperature of the electrolyte, if the measured potential difference has not reached the reference level during the time interval. The measuring and comparing process is then again carried out at this lower temperature and this is repeated until the temperature assumes such a value that the measured potential difference reaches the reference value during the time interval, this temperature value then being recorded on the indicator 24 as the critical temperature. In this embodiment of the invention, starting at a high temperature and progressively lowering the temperature, no activation of the specimen is needed.

Instead of measuring the potential difference between the test electrode 28 and the reference electrode 32 the current between the test electrode 28 and a counter electrode 30 can be measured at constant potential difference between the test and reference electrodes. After the initial temperature of the electrolyte 26 is adjusted, the potentiostat 12 is connected to the electrodes to keep the voltage between the test electrode and the reference electrode constant. In a procedure utilizing progressive increase of the temperature, the comparator 18 is disposed to trigger the programming unit 4 at the end of the interval determined by the time relay 22 for delivering to the regulator 6 a signal representing a higher temperature of the electrolyte if the measured current has not reached the reference level during the time interval. The measuring and comparing process is then carried out again at this higher temperature and this is repeated until the temperature assumes such a value that the measured current reaches the reference value during the time interval, this temperature value being recorded on the indicator 24 as the critical temperature.

When progressive decrease of the temperature of the electrolyte from a high initial temperature is used in which the current is high for the adjusted voltage, the comparator 18 is disposed to trigger the programming unit to deliver to the regulator 6 a signal representing a lower temperature of the electrolyte when the current reaches a preset reference value. After this new temperature has been adjusted, the measuring and comparing process is performed again and this is repeated until such a temperature is reached that the measured current no longer reaches the reference level before the end of the time interval determined by the time relay 22. At the end of the interval the programming unit 4 then activates an indicator 24 for recording this temperature as the critical temperature.

In this embodiment of the invention with a progressive decrease of the temperature no activation of the specimen is needed. The method according to this latter alternative is especially suitable for specimens in chloride containing solutions in which local corrosion attack often occurs where the current density is high.

As in the previous embodiment, the temperature is changed in pre-adjusted steps.

In practice, the apparatus according to the invention is preferably so constructed that any of the above described measuring procedures (measuring the potential at progressively increasing temperature, measuring the potential at progressively decreasing temperature, measuring the current at progressively increasing temperature and measuring the current at progressively decreasing temperature) can be freely chosen by simple switching.

The method and the apparatus according to the invention have a plurality of practical applications with considerable time savings and more accurate results being obtained as compared to prior art as mentioned above. A number of examples of the application of the invention is given below.

A. Acid solutions.

1. Recording of iso-corrosion diagrams in acid solutions.
2. Studies of the influence of flow rates on the appearance of the iso-corrosion diagrams. These studies are preferably carried out by rotating disc electrodes. It is not possible to carry out these studies by the prior art.
3. Studies of the influence of the oxygen content on the appearance of the iso-corrosion diagram. These studies are difficult to carry out by the prior art.
4. Comparison between different qualities in a special medium. To be able to do this comparison it is necessary to determine critical temperatures or concentrations. While it is very laborious and time consuming to do this by weight loss measurement, such measurement can quickly be done with the apparatus according to the invention.
5. Choice of materials in a special solution. The problem is the same as under point 4 above and the invention gives the same advantages.
6. Quality control. Measurements according to the invention can easily be standardized and used for quality control.
7. Studies of the influence on corrosion behaviour of existing material by variations in e.g. temperature, concentration and impurities in process solutions.

B. Neutral chloride containing solutions.

8. Determination of critical temperatures of pitting and crevice corrosion in a given solution.
9. Quick determination of critical pitting temperatures at varying flow rates. This is preferably performed by rotating disc electrodes.
10. Investigation of the influence of chloride content on the critical pitting temperature. Producing diagrams showing the variation of the critical pitting temperature vs. chloride content for standard steel of type SIS 2333 as well as for other kinds of material. This is intended to be used for selecting and developing materials.
11. Investigation of the influence by the pH-value on the critical pitting temperature.
12. Producing diagrams showing the dependence of the critical pitting temperature on the combined effect of two or more of the variables: pH, Cl$^-$—content and flow rate.
13. Quality control, which can easily be standardized, whereby the invention can be used for controlling manufacturing processes.

We claim:

1. An apparatus for determining the critical temperature for corrosion comprising:
   test, counter, and reference electrodes adapted to be submerged in an electrolyte,
   a temperature adjusting unit disposed for adjusting the temperature of the electrolyte to a predetermined value and a comparator unit arranged to compare the potential difference between the test and reference electrodes or the current intensity between the test and counter electrodes at constant potential difference between said test and reference electrodes with a preset reference voltage or current value as a means of detecting when the temperature of the electrolyte is equal to the critical temperature and to deliver a first output signal in response to this comparison to actuate an indicator when the comparison indicates that the temperature of the electrolyte is equal to the critical temperature and to deliver a second signal to trigger the temperature adjusting unit to alter the temperature of the electrolyte for another comparison test when the comparison indicates that the electrolyte temperature is not equal to the critical temperature.

2. The apparatus according to claim 1, wherein the temperature adjusting unit comprises a programming unit, which is arranged to receive the output signal from the comparator unit and in response to this signal to either actuate the indicator or trigger the temperature adjusting unit to alter the temperature of the electrolyte.

3. The apparatus according to claim 2, wherein the temperature adjusting unit comprises a regulator, which is disposed, on one hand, to receive from the programming unit a signal representing a desired value of the temperature of the electrolyte and, on the other hand, to receive from a temperature transmitter a signal representing the actual temperature of the electrolyte and in response to these signals control the heat supply to the electrolyte so that its temperature assumes the desired value.

4. The apparatus according to claim 1 wherein the comparator unit is arranged to control the temperature adjusting unit to increase the temperature of the electrolyte by a predetermined, constant amount, when said potential difference reaches the reference voltage value and in that a first timing unit is disposed to determine, for each temperature, a maximum time interval for the measurement and the comparison, the comparator unit delivering said actuating signal to the indicator at the end of said time interval if the measured potential difference has not reached the reference value.

5. The apparatus according to any one of the claims 1 to 3, wherein a first timing unit is disposed to determine a maximum time interval for the measurement and the comparison in the comparator unit and in that the comparator unit is arranged to control the temperature adjusting unit to decrease the temperature of the electrolyte by a predetermined, constant amount at the end of each time interval, if the potential difference does not reach the reference value during the interval, the comparator unit delivering said actuating signal to the indicator when the measured potential difference reaches the reference value.

6. The apparatus according to claim 1 wherein a potentiostat is arranged to maintain the voltage between the test and reference electrodes constant.

7. The apparatus according to claim 6, wherein a first timing unit is disposed to determine a maximum time interval for the measurement and comparison in the comparator unit and in that the comparator unit is arranged to control the temperature adjusting unit to increase the temperature of the electrolyte by a predetermined, constant amount at the end of each time interval, if the measured current does not reach the reference value during the interval, said comparator unit delivering said actuating signal to the indicator when the measured current reaches the reference value.

8. The apparatus according to claim 6, wherein the comparator unit is disposed to control a temperature adjusting unit to decrease the temperature of the electrolyte by a predetermined, constant amount, when the current reaches said reference value, and in that a first timing unit is arranged to determine a maximum time interval for the measurement and the comparison for each temperature, the comparator unit delivering said actuating signal to the indicator at the end of said time interval if the measured current has not reached the reference value.

9. The apparatus according to any one of the claims 1 to 4, and 6 to 8 wherein
means are connected to the comparator unit for adjusting the reference voltage or current value.

10. A method of determining critical temperatures for corrosion wherein
the temperature of an electrolyte in which test, counter, and reference electrodes are submerged, is adjusted to a predetermined value;
whereafter the potential difference between the test and reference electrodes or the current intensity between the test and counter electrodes at constant potential difference between the test and reference electrodes is measured and compared with a preset reference voltage or current value,
said measuring and comparison process being interrupted when the measured potential difference or the current reaches the reference value;
whereupon the temperature of the electrolyte is altered and the measuring and comparison process is again carried out;
the preceding steps being repeated until the temperature is such that the measuring potential difference or the current does not reach said reference value during a predetermined time interval;
the temperature of the electrolyte then being recorded as the critical temperature.

11. A method of determining critical temperatures for corrosion wherein
the temperature of an electrolyte in which test, counter, and reference electrodes are submerged, is adjusted to a predetermined value;
whereafter the potential difference between the test and reference electrodes or the current intensity between the test and counter electrodes at constant potential difference between the test and reference electrodes is measured and compared with a preset reference voltage or current value, said measuring and comparison process being carried out during a predetermined time interval;
whereafter, if the measured potential difference or the current has not reached said reference value during said time interval, the temperature of the electrolyte is altered at the end of the interval;
whereupon the measuring and comparison process is again carried out;
the preceding steps being repeated until the temperature is such that the measured potential difference or the current reaches the reference value during the time interval, the temperature of the electrolyte then being recorded as the critical temperature.

12. The method according to claim 10 or claim 11 wherein the temperature of the electrolyte is always increased in predetermined steps, or always decreased in predetermined steps.

13. The method as claimd in claim 10 or claim 11 wherein the temperature of the electrolyte is always increased in predetermined steps or always decreased in predetermined steps,
said predetermined steps being of constant magnitude.

14. The method as claimed in claim 10 or claim 11 wherein the test electrode is activated between successive measuring and comparison process steps.

* * * * *

UNITED STATES PATENT AND TRADEMARK OFFICE
CERTIFICATE OF CORRECTION

PATENT NO. : 4,214,951

DATED : July 29, 1980

INVENTOR(S) : Sven-Olof Bernhardsson and Stig A. Alfredsson

It is certified that error appears in the above-identified patent and that said Letters Patent are hereby corrected as shown below:

Column 1, line 58, "comarison" should read --comparison--.

Column 2, line 28, the semicolon after "electrolyte" should not be there;
line 29, "valve" should read --value--.

Column 3, line 20, "acutal" should read --actual--;
lines 35 and 36, "refernce" should read --reference--.

Column 5, line 44, "by" should read --of--.

Column 7, line 27, "measuring" should read --measured--.

Signed and Sealed this

Eighteenth Day of November 1980

[SEAL]

Attest:

SIDNEY A. DIAMOND

Attesting Officer     Commissioner of Patents and Trademarks